United States Patent
Lapointe et al.

(10) Patent No.: US 8,663,621 B2
(45) Date of Patent: Mar. 4, 2014

(54) **IDENTIFICATION AND SYNTHESIS OF A MALE-PRODUCED PHEROMONE FOR THE NEOTROPICAL ROOT WEEVIL *DIAPERPES ABBREVIATUS* (COLEOPTERA: CURCULIONIDAE)**

(71) Applicant: The United States of America, as Represented by the Secretary of Agriculture, Washington, DC (US)

(72) Inventors: Stephen L Lapointe, Vero Beach, FL (US); Ashot Khrimian, Rockville, MD (US); Joseph C Dickens, Elicott City, MD (US); Peter Edmund Alan Teal, Gainesville, FL (US); Fatma Kaplan, Gainesville, FL (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 13/745,509

(22) Filed: Jan. 18, 2013

(65) Prior Publication Data
US 2013/0189222 A1  Jul. 25, 2013

Related U.S. Application Data

(60) Provisional application No. 61/589,924, filed on Jan. 24, 2012.

(51) Int. Cl.
*C07C 69/533* (2006.01)
*A01M 1/14* (2006.01)

(52) U.S. Cl.
USPC .............................. 424/84; 424/405; 43/132.1

(58) Field of Classification Search
USPC ........................................................... 424/84
See application file for complete search history.

(56) References Cited

U.S. PATENT DOCUMENTS 8,066,979 B1    11/2011   Dickens et al.

OTHER PUBLICATIONS

Ambrogi, B.G. et al., "Feromônios De Agregação Em Curculionidae (Insecta: Coleoptera) E Sua Implicação Taxonômica" | ["Aggregation Pheromone in Curculionidae (Insecta: Coleoptera) and Their Taxonomic Implication"] (2009) Quim. Nova 32(8):2151-2158.

*Primary Examiner* — David J Blanchard
*Assistant Examiner* — John P Nguyen
(74) *Attorney, Agent, or Firm* — John D. Fado; David L. Marks (57) ABSTRACT

An unsaturated hydroxyl-ester pheromone for the neotropical root weevil *Diaprepes abbreviatus* has been isolated, identified and synthesized. It is useful for trapping the weevil to reduce or prevent damage to plants.

7 Claims, 4 Drawing Sheets

IDENTIFICATION AND SYNTHESIS OF A MALE-PRODUCED PHEROMONE FOR THE NEOTROPICAL ROOT WEEVIL *DIAPERPES ABBREVIATUS* (COLEOPTERA: CURCULIONIDAE)

CROSS-REFERENCE TO RELATED APPLICATION

This application claims the benefit of U.S. Provisional Application No. 61/589,924, filed on Jan. 24, 2012 which is herein incorporated by reference in its entirety.

FIELD OF THE INVENTION

This invention relates to a pheromone for attracting female *Diaprepes abbreviatus* root weevil, a kit containing the pheromone, and to methods for using the pheromone to attract and trap female weevils.

BACKGROUND OF THE INVENTION

The root weevil *Diaprepes abbreviatus* (L.), is a major pest of citrus in the Caribbean and Florida. Prior to the 1960's, *D. abbreviatus* was reported only in the Caribbean. Because multiple phenotypic populations occur on Puerto Rico it is suggested that *D. abbreviatus* originated in Puerto Rico (Lapointe 2004). Since its discovery near Apopka, Fla. in 1964, it has spread to Louisiana, Texas and California. There is no geographic or climatic barrier to prevent the southern movement of this insect to Mexico, Mesoamerica and South America (Lapointe et al. 2007).

This migration is of concern because this insect is destructive. Adult beetles of *D. abbreviatus* oviposit and feed on leaves of a wide range of hosts including more than 270 species of plants in 59 plant families. Feeding by adults on leaves causes a characteristic notching pattern; however, the larval stage causes the most serious damage. Neonate larvae fall to the ground and burrow into the soil where they feed on progressively larger roots over a period of months as they grow. Larval feeding on citrus tree roots can eventually girdle the crown area of the root system, killing the host plant. When larval development is completed, adults emerge from the soil to feed upon foliage where aggregation, mating and oviposition take place. In certain citrus growing areas, root damage by larval *D. abbreviatus* creates favorable conditions for species of *Phytophthora*, a very serious and often lethal plant pathogen, to invade roots and further hasten the decline of trees.

In Florida, citrus growers spend up to $400/acre for combined control of *D. abbreviatus* and *Phytophthora*. In 2009, it was estimated that the total increase in costs per ton due to the establishment and spread of Diaprepes root weevil in California would be $53.60 for orange, $45.20 for grapefruit, $42.50 for lemon and $200.00 for avocado. In view of the negative economic impact caused by the feeding of this insect and in view of the fact that there appear to be no natural barriers to important agricultural citrus growing areas, attractants that will allow for the monitoring, tracking, trapping and destroying of this insect have been sought.

*Diaprepes abbreviatus* has been placed in the subfamily Entiminae of the Curculionidae (Marvaldi et al. 2002) Within the superfamily Cu rculionoidea (weevils) the majority of attractants or pheromones identified to date are long-range, male-produced aggregation pheromones (Seybold and Vanderwel 2003, Ambrogi et al. 2009). Aggregation of *D. abbreviatus* adults and the occurrence of so-called "party trees" have been observed (Wolcott 1936). Schroeder (1981) suggested a male-produced pheromone attracted females and a female-produced pheromone attracted males. Beavers et al. (1982) showed in laboratory tests that male and female *D. abbreviatus* were significantly attracted to the frass of the opposite sex. Jones and Schroeder (1984) demonstrated a male-produced pheromone in the feces that attracted both sexes. A pheromone responsible for arrestment behavior was suggested by Lapointe and Hall (2009). U.S. Pat. No. 8,066,979 to Dickens et al. showed for the first time that *D. abbreviatus* adults have olfactory receptors for secondary plant metabolites that belong to diverse chemical groups: (a) alcohol and aldehyde monoterpenes (e.g., linalool, citronellal, nerol, and trans-geraniol), (b) green leaf volatiles (e.g., cis-3-hexen-1-ol and trans-2-hexen-1-ol), and (c) an aromatic monoterpenoid (e.g., carvacrol). Otálora-Luna et al. (2009) identified by gas-chromatograph electroantennograph detection (GC-EAD) a number of plant volatiles from citrus leaves that elicited antennal response in *D. abbreviatus*. Such kairomones may act in concert with a pheromone to attract conspecifics to a suitable food source (Dickens 1990). Only one pheromone, that of *Sitona lineatus* (4-methyl-3,5-heptanedione), an aggregation pheromone, has been isolated from the Entiminae (broad-nosed weevils) (Blight et al. 1984). Blight and Wadhams (1987) suggested that *S. lineatus* produces its aggregation pheromone in the spring and that the pheromone activity is synergized by host plant volatiles including (Z)-3-hexen-1-ol and linalool.

Despite reports, no compound has been identified and isolated from *D. abbreviatus* that is responsible for attraction in this species. Thus a pheromone has long been sought for this species.

BRIEF SUMMARY OF THE INVENTION

In accordance with the present invention, an unsaturated hydroxy ester pheromone collected from the headspace and feces of male *Diaprepes abbreviatus* was isolated, identified and synthesized. The pheromone, methyl (E)-3-(2-hydroxyethyl)-4-methyl-2-pentenoate, was discovered by gas chromatography-coupled electroantennogram detection (GC-EAD) and identified by gas chromatography-mass spectrometry (GC-MS) and nuclear magnetic resonance spectroscopy (NMR). The synthetic protocol yielded a 86:14 mixture of methyl (E)-3-(2-hydroxyethyl)-4-methyl-2-pentenoate and an inactive methyl (Z)-3-(2-hydroxyethyl)-4-methyl-2-pentenoate along with a lactone decomposition product. The activity of the synthetic E isomer was confirmed by GC-EAD, GC-MS, NMR and behavioral assays. No antennal response was observed to the Z isomer or the lactone. In a two-choice olfactometer bioassay, female *D. abbreviatus* moved upwind towards the synthetic pheromone or a source of natural pheromone more often as compared to clean air. Males showed no clear preference for the synthetic pheromone.

BRIEF DESCRIPTION OF THE SEVERAL VIEWS OF THE DRAWING

FIGS. 3A and 3B show the CI and EI spectra, respectively, of the natural pheromone obtained from the headspace above male *Diaprepes abbreviatus*. C shows the EI spectrum for the synthetic pheromone.

DETAILED DESCRIPTION OF THE INVENTION

For purposes of the invention, the following are definitions of certain terms to be used hereinafter.

As used in the specification and claims, the singular form "a", "an", and "the" include plural references unless the context clearly dictates otherwise. For example, the term "a cell" includes a plurality of cells, including mixtures thereof.

The term isolated, purified, or biologically pure as used herein, refer to material that is substantially or essentially free form components that normally accompany it as found in its native state. In an exemplary embodiment, purity and homogeneity are determined using analytical chemistry techniques such as polyacrylamide gel, electrophoresis, or high performance liquid chromatography.

Unless defined otherwise, all technical and scientific terms used herein have the same meaning as commonly understood by one of ordinary skill in the art to which the invention belongs. The terms "about" and "approximately" are defined as plus or minus ten percent; for example, about 100° F. means 90° F. to 110° F. Although any methods and materials similar or equivalent to those described herein can be used in the practice or testing of the present invention, the preferred methods and materials are now described.

We report here the isolation, identification and synthesis of a pheromone from male *D. abbreviatus* that attracts female *D. abbreviatus*. Isolation and identification of the pheromone was obtained from adult *D. abbreviatus* weevils from a laboratory colony maintained at the United States Horticultural Research Laboratory, a unit of the Agricultural Research Service of the USDA, located in Ft. Pierce, Fla. These insects have been supplemented annually with field-collected adults. Neonate larvae were placed on an artificial diet (product no. F1675, Bio-Serv, Inc., Frenchtown, N.J.) and reared as described by Lapointe et al. (2008). Adults were held in separate 60×60×60 cm mesh cages and fed young citrus leaves (*Citrus macrophylla* Wester). Males and females were caged separately. Thereafter groups of about 20 to 30 adults of about 4 to 6 weeks of age were held separately without food, but allowed water via a water-saturated cotton dental wick for approximately 24 hours prior to aeration assays. After the assay, adults were returned to their respective cages and provided food and water. Individual unmated adults were used in tests no more than once a week over a period of about 3 months. Cohorts of known age were caged separately.

Example 1

In a first assay employed to find an attractive chemical of insect origin, a gas chromatograph-coupled electroantennogram detection (GC-EAD) system was used to analyze male aeration samples. This system included an Agilent 7890A GC equipped with a split/splitless injector, an HP-1 capillary column (approximately 30 m×0.32 mm×0.25 μm, Agilent Technologies, Inc., Santa Clara, Calif., USA), a post column glass Y-tube (Supelco, Bellefonte, Pa., USA) splitter for dividing column effluent in an approximately 1:1 ratio between a flame ionization detector (FID) and a heated (200° C.) EAD transfer line. Two lengths of deactivated column (approximately 0.32 mm ID) were used to carry effluent to the FID and EAD port after the split. At the start of GC-EAD runs, the GC oven temperature was held at about 35° C. for 3 minutes and then increased to about 260° C. at a rate of about 15° C./min and held at about 260° C. for about 10 min. Injector and FID temperatures were set at about 220° C. and about 300° C., respectively. Splitless injection was used with helium as the carrier gas at a flow rate of about 2.3 ml/min. A heated transfer line emptied into a charcoal-filtered, humidified air stream (about 200 ml/min at about 30 cm/sec) that carried the effluent over an antennal preparation. The antennal preparation can be made by plucking the antenna from either a male or female insect (grasping it firmly at the base of the antenna near the head with fine forceps) and placing the antenna between two metal electrodes of a Universal EAG probe, to which small amounts of salt-free electrode gel (Spectra 360, Parker Laboratories, Fairfield, N.J., USA) had been applied. The probe was connected to a type PRG-2 amplifier (Universal EAG probe, Syntech, Hilversum, The Netherlands). The humidified air stream was directed to pass over the antennal preparation generating a signal. The effluent sent through to the FID line also caused a signal to be generated and signals from the amplifier and the FID were conditioned using a Syntech IDAC-2 interface. EAG and FID signals acquired from the IDAC-2 were displayed and stored on a computer running the GC-EAD 2011 software program (Syntech).

Figure 2:
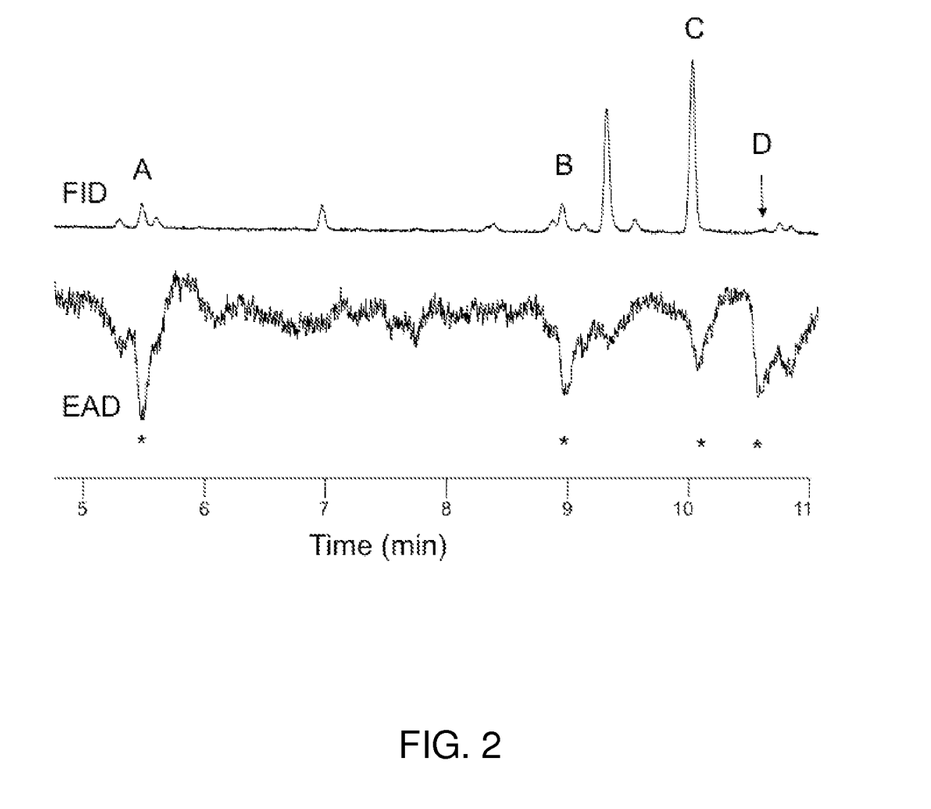
FIG. 2 shows simultaneous gas chromatogram (FID) and electroantennogram detection (EAD) of a male *Diaprepes abbreviatus* antenna responding to a hexane extract of headspace volatiles collected from adult males and citrus leaves. Compounds A-C correspond to the plant volatiles linalool, geraniol and citral, respectively; compound D is male-derived. Asterisks indicate consistent antennal responses.

As shown in FIG. 2, a single peak of a chemical compound, labeled D, of insect origin was detected by GC-EAD from aerations of male weevils. No response was observed at the retention time observed for compound D from either male or female antennae when exposed by GC-EAD to aerations of female weevils or citrus leaves alone (data not shown). The aerations from male weevils elicited consistent antennal responses from both male and female *D. abbreviatus*. Although the amount of this compound in 24-hour aerations of ten *D. abbreviatus* males was sufficient to elicit a response from male and female antennae by GC-EAD, the small amounts approached the detection limit of the GC as shown in FIG. 2. Nevertheless, as stated above, the effluent containing aeration samples elicited consistent antennal responses from both female and male *D. abbreviatus*. Peaks A through C of FIG. 2 correspond respectively to the plant volatiles linalool, geraniol, and geranial, and Peak D of FIG. 2 corresponds to an insect-generated chemical. The asterisks in FIG. 2 indicate positive antennal responses typical of those consistently produced in multiple runs with multiple antennae.

Example 2

In a separate assay to further identify the insect-generated compound, multiple groups of approximately 20 to 30 male and female *D. abbreviatus*, held separately, were placed in separate glass aeration chambers without plant material and provided with a continuous flow (about 500 ml/min) of filtered, humidified air for about 24 hr at about 27° C. in an environmental chamber (about 12:12 hr L:D). Volatiles from the headspace were collected on Super Q filters (Alltech Deerfield, Ill., USA) connected to the exit port of the aeration chambers. After collection, the filters were eluted with approximately 500 µl of methylene chloride. Separate from the volatile collections, the accumulated feces in the aeration chambers at the end of the about 24-h collection period were collected by washing the chambers with a minimum amount of methylene chloride. The resulting extract was filtered and concentrated under nitrogen.

As an initial purification, methylene chloride ($CH_2Cl_2$) eluates (about 200 µl) from the Super Q filters and washes of the aeration chambers were passed through Supelclean LC-SI solid phase extraction (SPE) columns containing approximately 200 mg of packing (Supelco, Bellefonte, Pa.) previously conditioned with about 15 ml of methylene chloride. The methylene chloride eluates plus a filter wash of about 2 ml of methylene chloride were saved to check for the presence of biologically active insect-derived compound. The SPE column was eluted with about 2 ml each of pentane containing approximately 15% ethyl acetate (EtOAc), approximately 30% ETOAc and approximately 50% ETOAc. The three SPE column fractions and the saved eluates were analyzed by EI GC-MS (electron impact) for the presence of the biologically active insect-derived compound. Only the approximately 15% EtOAc fraction contained the compound of interest. This fraction was concentrated to about 100 µl under a fine stream of $N_2$ and subjected to fractionation by preparative GC. Initial fractionation was accomplished using an Agilent 6890 GC® with cool-on-column injector and fitted with an approximately 20 cm length of deactivated fused silica attached to an approximately 30 m×0.53 mm inner diameter (approximately 0.5 µm film thickness) DB1 column. The analytical column was split using a "Y" capillary connector between equal lengths of approximately 0.1 mm inner diameter and approximately 0.25 mm inner diameter lengths of deactivated fused silica column. The effluent from the approximately 0.1 mm column (about 13.8%) went to the GC FID while the 0.25 mm column (about 86.2%) exited the wall of the GC and into the heated block (200° C.) of a Brownlee-Silverstein collector (Brownlee and Silverstein 1968). Samples (approximately 10 µl each) were injected onto the column at an initial temperature of about 30° C., after about 2 min the oven temperature was increased to a final temperature of about 225° C. at about 10° C./min. The fractions were collected in approximately 30 cm cooled glass capillaries (Brownlee and Silverstein 1968). After collection, samples were recovered by washing the capillaries with 3 aliquots of approximately 25 µl of methylene chloride. Fractions were analyzed by GC-MS for the presence of the compounds having daughter ions at approximately m/z 154, 142 and 140, all of which maximize within about 0.01 min of each other. These fractions from replicated collections to amass sufficient material for NMR analysis were combined, concentrated and re-fractionated using a DB35 column (approximately 30 m×0.53 mm id, approximately 0.5 µm film thickness) as above. The fractions from this separation were eluted from capillaries using deuterated chloroform ($CDCl_3$ Cambridge isotopes 99.96%), analyzed by coupled gas chromatography-mass spectrometry (GC-MS). The fractions containing the compound having the 172 MW were combined, concentrated under $N_2$ and submitted form NMR analysis.

Figure 3A:
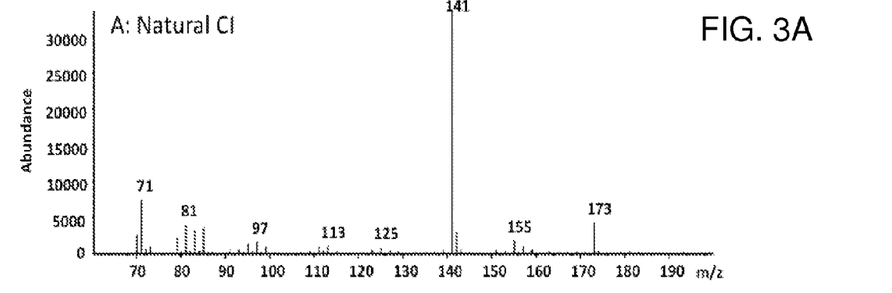
FIGS. 3A-3C are graphs showing chemical ionization (CI) and electron impact (EI) ionization mass spectra of the natural and synthetic pheromone methyl (E)-3-(2-hydroxyethyl)-4-methyl-2-pentenoate.
Figure 3B:
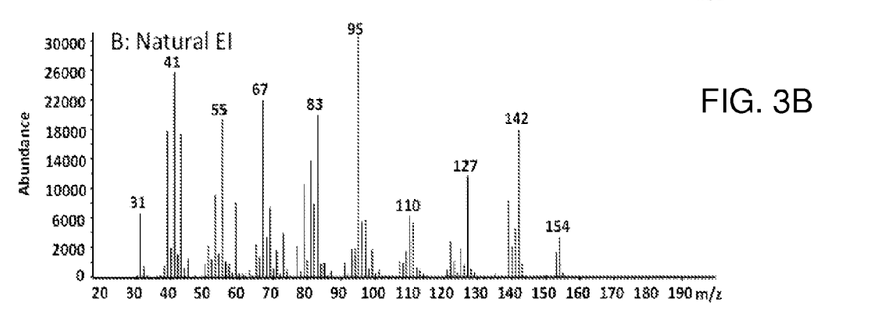

GC-MS was conducted using instruments operated in the electron impact (EI) and chemical ionization (CI) mode. EI spectra were obtained using an Agilent 5973 MS interfaced to a 6890 GC equipped with a cool on-column injector. The injector was fitted with an about 10 cm length of about 0.5 mm id deactivated fused silica tubing connected to about a 1 m (about 0.25 mm id) length of deactivated fused silica tubing as a retention gap. The retention gap was connected to an about 30 m×0.25 mm id with an about 0.25 µm coating thickness DB5MS® analytical column. The temperature program was: initial oven and injector temperatures=about 30° C., about 5 min; oven and injector temperatures increased at about 10° C./min; final temperature=about 225° C. Spectra were obtained between 60-300 atomic mass units. Chemical ionization spectra were obtained using an Agilent 5975 MS interfaced to a 7890 GC. The GC was equipped with a cool on-column injector fitted with retention gaps as above. The analytical column used was an about 30 m×0.25 mm id, about 0.25 µm coating thickness DB1MS®. The GC was operated using the same program as for EI spectra and the CI spectra were obtained by scanning from m/z 60-300 using isobutane as a reagent gas. Tentative chemical identification of the putative pheromone peak was deduced from fragmentation patterns obtained from both EI- and CI-MS analyses (FIGS. 3A and 3B).

The peak corresponding to the putative pheromone was also recovered by washing the glass aeration jars to recover the excreta (frass) of males in methylene chloride. Combining multiple collections of the headspace over males provided sufficient material to obtain CI and EI mass spectra (FIGS. 3A and 3B). Initial GC analyses indicated the presence of numerous compounds eluting in the area of the peak with GC-EAD activity (FIG. 2). EI GC-MS analyses indicated that several of these, including the EAD active, had approximately m/z=154 in common and fragmentation patterns corresponding to monoterpene alcohols. Although the EI mass spectrum of the compound of interest showed an approximately m/z 154 as a potential molecular ion (FIG. 3B), the additional presence of an approximately m/z 142 (m/z 154-12 amu) fragment indicated either a mixture, or that approximately m/z 154 might not be the molecular ion. A maximization of approximately m/z 140, 142 and 154 within ±0.01 min suggested all ions to be fragments of the same molecular ion and thus m/z 154 could not be a molecular ion.

CI-MS analysis (FIG. 3A) gave clear M+1 ions at approximately m/z 173, thus supporting a molecular weight of approximately 172 Daltons. In addition, the CI analysis also gave a base peak at approximately m/z 141 (M+1-$CH_3OH$) and approximately m/z 155 (M+1-18), thus approximately m/z 154 in the EI spectra being the corresponding M-18 fragment. The CI analysis did not give any direct explanation of the approximately m/z 142 fragment in the EI spectra, but the loss of about 30 amu (m/z 172-m/z 142) suggested a long range proton transfer to a carbonyl group followed by a neutral loss of $CH_2$=O characteristic of a hydrocarbon chain with a terminal alcohol as well as a carbonyl. This was congruent with a methyl ester as suggested by the (M+1-$CH_3OH$) loss in the CI spectrum. A characteristic neutral loss of about 32 amu was also seen in the EI spectra (approximately m/z 142-m/z 110), thereby supporting the structure of a methyl ester. Furthermore, the neutral loss of about 15 amu (approximately m/z 142-m/z 127 as well as approximately m/z 110-m/z 95) suggested the presence of a methyl branch. Thus, the fragmentation patterns indicated a formula of $C_9H_{16}O_3$ with 2 degrees of unsaturation, the presence of a methyl ester and at least one methyl branch in addition to a terminal C—OH. Further aerations of groups of up to about 30 males and fractionation by preparative GC using both polar and nonpolar capillary columns resulted in collection of a sufficient amount of the pheromone for NMR analysis.

Example 3

Fractions containing the insect derived chemical were combined, concentrated under $N_2$ and submitted for NMR analysis. One and two-dimensional NMR spectroscopy, including double-quantum filtered correlation spectroscopy (dqCOSY), heteronuclear single-quantum coherence (HSQC), heteronuclear multiple-bond correlation (HMBC) and Nuclear Overhauser Enhancement Spectroscopy (NOESY) were used to characterize the pheromone. NMR spectra of the natural product were acquired at about 27° C. using an approximately 5-mm TXI cryoprobe and a Bruker Avance II 600 console (about 600 MHz for about 1H, approximately 151 MHz for $^{13}$C). The combined fractions containing the insect-derived compound were dissolved in approximately 150 μl of deuterated chloroform (CDCl$_3$) (Cambridge Isotope Laboratories Inc.) and placed in an about 2.5 mm NMR tube (Norell). Residual chloroform (CHCl$_3$) was used to reference chemical shifts to δ(CHCl$_3$)=approximately 7.26 ppm for 1H and δ(CHCl$_3$)=approximately 77.36 ppm for $^{13}$C (Gottlieb et al. 1997). Bruker Topspin 2.0 and Mestrelab MNova NMR (Mestrelab Research SL) software packages were used to process NMR spectra. $^1$H NMR spectra of synthetic materials including a NOE difference spectrum for 1E were obtained on a Bruker AVIII-600 MHz spectrometer. Pheromone NMR analysis is set forth in Table 1.

TABLE 1

HMBC and NOESY NMR spectroscopic data for the putative pheromone of *Diaprepes abbreviatus* in CDCl$_3$

⌒ $^1$H—$^{13}$C HMBC
— $^1$H NOESY

| Position | δ $^{13}$C [ppm] | δ $^1$H [ppm] | J coupling constants [Hz] | HMBC correlations | NOESY |
|---|---|---|---|---|---|
| 1 | 169.0* | — | — | — | — |
| 2 | 115.5 | 5.83 | s | | 1.10 |
| 3 | 166.9* | — | — | — | — |
| 4 | 36.35* | 2.43 | m J = 6.7 | | |
| 5 and 6 | 21.7 | 1.10 | d, J = 6.8 | C4, C3 | 5.83 and 2.84 |
| 7 | 35.2 | 2.84 | t, J = 6.4 | C2, C3, C4, C8 | 1.10 |
| 8 | 62.5 | 3.8 | br t J = 6.3 | | — |
| 9 | 51.7 | 3.7 | s | C1 | |

$^1$H (600 MHz), $^{13}$C (151 MHz),.
Chemical shifts referenced to δ(CHCl$_3$) = 7.26 ppm for $^1$H and δ(CHCl$_3$) = 77.36 ppm for $^{13}$C.
Coupling constants are given in Hertz [Hz].
*The $^{13}$C chemical shifts are deduced from HMBC; others are deduced from HSQC.
$^1$H chemical shifts are deduced from 1D $^1$H NMR Example 4

Figure 1:
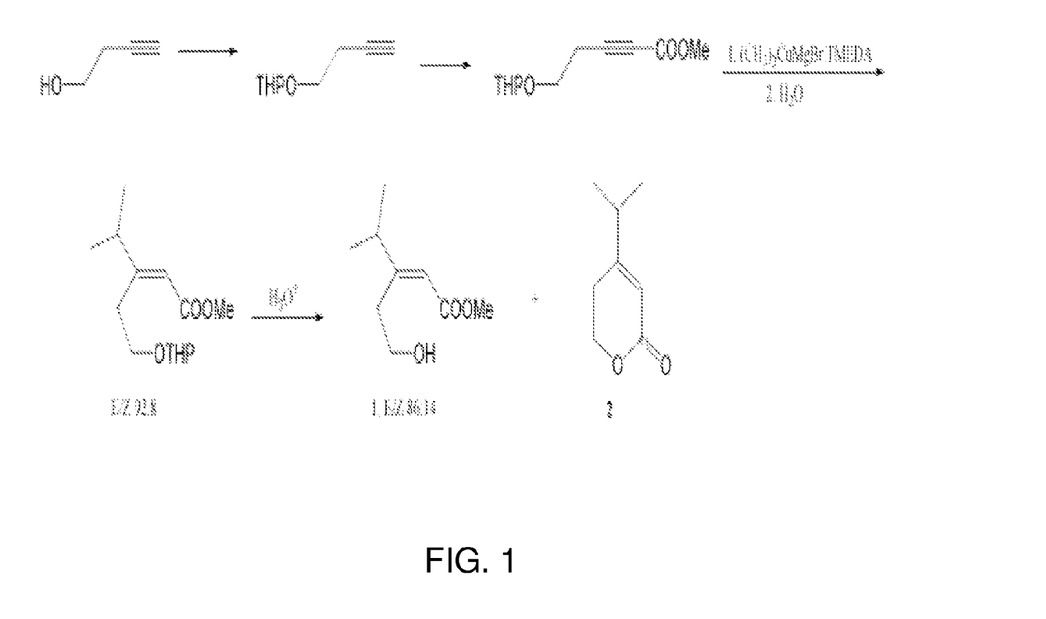
FIG. 1 is a diagram showing the synthetic route for the production of methyl (E)-3-(2-hydroxyethyl)-4-methyl-2-pentenoate (1), and related compounds.

Methyl (E)-3-(2-hydroxyethyl)-4-methyl-2-pentenoate was synthesized according to scheme shown in FIG. 1. Unless otherwise specified all reagents and solvents were purchased from Aldrich Chemical Co. Tetrahydropyranyl ether (THP) protection of 3-butyn-1-ol was conducted following a procedure by Rama Rao et al. (1986). A solution of 3-butyn-1-ol (approximately 14.0 g, approximately 0.2 mol) in methylene chloride (approximately 75 ml, dried by distillation from CaH$_2$) was placed in a flask under N$_2$. The mixture was cooled to approximately 0° C., and pyridine p-toluenesulfonate (approximately 0.28 g) was added. 3,4-Dihydro-2H-pyran (about 20.1 ml) was added via a dropping funnel maintaining the temperature between approximately 0 and approximately 5° C. The mixture was stirred at this temperature for about 1 h, then warmed to about 25° C. and stirred for additional about 2 h. Thin layer chromatography (silica gel, hexanes/ethyl acetate, approximately 3:1) showed that the reaction was complete. The reaction mixture was taken into cold water (approximately 70 ml) and transferred to a separatory funnel. The layers were separated and the aqueous phase was extracted with methylene chloride. Combined organic extracts were washed with NaHCO$_3$ (aq), brine, and dried with Na$_2$SO$_4$ (anhydrous). Distillation produced approximately 23 g of THPO-protected 3-butyn-1-ol with a by of about 50-55° C./4 mm Hg with GC-MS (m/z, relative intensity): 153 (2, M$^+$-1), 99 (9), 85 (100), 79 (9), 67 (20), 53 (42), 41 (33). The mass spectrum matched the spectrum presented in the NIST MS library for this intermediate compound.

A solution of the THPO-ether of 3-butyn-1-ol (approximately 2.88 g, approximately 18.7 mmol) in THF (about 40 ml, dried with sodium benzophenone ketyl) was placed under N$_2$ into a four-neck flask and cooled to about −75° C. Butyl lithium (approximately 18.7 mmol, approximately 9.4 ml of approximately 2.0 M in hexanes) was added slowly via a dropping funnel at about −75° C. The mixture was stirred at this temperature for about 30 min, and then methyl chloroformate (ClCOOMe, about 1.4 ml, about 18.7 mmol) was added. The resulting mixture was stirred at about −75° C. for about 30 min, then slowly warmed to about 25° C. in approximately 2 h and poured into a cold saturated NH$_4$Cl solution. The organic material was extracted with hexanes/ether, approximately 1:1. The combined extracts were washed with brine and dried. After removal of the solvent on a rotary evaporator, the remainder was flash chromatographed on silica gel with hexanes/ethyl acetate, approximately 4:1, to isolate methyl 5-(tetrahydro-2H-pyran-2-yloxy)-2-pentynoate (approximately 2.5 g, approximately 65%). GC-MS (m/z, relative intensity): 211 (1, M$^+$-1), 157 (4), 153 (3), 142 (4), 125 (18), 113 (9), 109 (11), 85 (100), 79 (41), 67 (18), 55 (16), 41 (26). $^1$H NMR (CDCl$_3$): 1.50-1.64 (m, 4H), 1.72 (m, 1H), 1.83 (m, 1H), 2.66 (t, J=6.6 Hz, 2H, H-4), 3.53 (m, 1H, H-5A), 3.62 (dt, J=9.8, 7.5 Hz, 1H, H-5B), 3.77 (s, 3H, OCH$_3$), 3.87 (m, 2H), 4.65 (br t, J=4.0 Hz, 1H, OCHO). $^1$H NMR data were in agreement with data obtained for this compound in CCl$_4$ (Rama Rao et al. 1986).

Freshly purchased copper iodide (CuI, approximately 1.97 g, approximately 12.2 mmol) was placed under N$_2$ in a four-neck flask. Dry tetrahydrofuran (THF) (about 35 ml) was added, followed by N,N,N',N'-tetramethylethylenediamine (about 2.76 ml). The mixture was stirred at room temperature until a green-yellow solution was obtained and then cooled to about −70° C., upon which a green suspension was formed. Isopropylmagnesium chloride solution (approximately 12.3 mmol; about 6.1 ml of approximately 2.0 M in tetrahydrofuran (THF) was added slowly, whereupon a green suspension became colorless then turned brown. The mixture was stirred at about −70° C. for about 1 h, then methyl 5-(tetrahydro-2H-pyran-2-yloxy)-2-pentynoate (approximately 1.3 g, approximately 6.1 mmol) dissolved in dry THF (about 5-10 ml) was added. The resultant mixture was stirred at about −70° C. for about 3 h and quickly poured into an ice-cold mixture of saturated NH$_4$Cl and hexanes/ether, approximately 5:1. The organic layer was separated, and the aqueous layer was extracted with hexanes/ether, approximately 5:1. The combined organic extracts were thoroughly washed with saturated $NH_4Cl$ solution until no blue color was seen. The organic extract was dried and concentrated. Flash chromatography with hexanes/ethyl acetate, approximately 5:1, afforded methyl 4-methyl-3-[2-(tetrahydro-2H-pyran-2-yloxy)ethyl]-2-pentenoate (approximately 1.3 g, approximately 85%) as an approximately 92:8 mixture of E and Z isomers as judged from GC-MS analysis. GC-MS (E isomer, m/z, relative intensity): 172 (2), 171 (3), 155 (32), 142 (8), 141 (6), 139 (6), 95 (17), 85 (100), 67 (16), 57 (10), 55 (11), 43 (11), 41 (16). GC-MS (Z isomer, m/z, relative intensity): 172 (4), 155 (3), 154 (8), 142 (8), 141 (2), 139 (4), 123 (6), 95 (23), 85 (100), 67 (17), 57 (10), 55 (12), 43 (11), 41 (17). $^1H$ NMR (400 MHz, $C_6D_6$, δ): 0.86 (d, J=8.0 Hz, E isomer), 0.86 (d, J=8.0 Hz, Z isomer), 1.20-1.42 (m, 4H), 1.55-1.62 (m, 2H), 1.70-1.82 (m, 1H), 2.18-2.31 (m, 1H), 3.02-3.18 (m, 2H), 3.41 (s, $OCH_3$), 3.67-3.73 (m, 1H), 3.81-3.88 (m, 1H), 4.04-4.11 (m, 1H), 4.39 (septet, J=8.0 Hz, H-4, Z isomer), 4.52 (t, J=4.0 Hz, OCHO, Z isomer), 4.66 (t, J=4.0 Hz, OCHO, E isomer), 5.83 (br. s, H-2, E isomer), 5.86 (br. s, H-2, Z isomer). $^{13}C$ NMR (101 MHz, $C_6D_6$, δ, E isomer): 20.0, 21.7 (two carbons), 26.3, 31.4, 32.9, 37.3, 50.9, 61.9, 67.3, 98.8, 115.1, 167.2, 167.8.

Methyl 4-methyl-3-[2-(tetrahydro-2H-pyran-2-yloxy) ethyl]-2-pentenoate (approximately 256 mg, approximately 1 mmol) was stirred with p-toluenesulfonic acid hydrate (approximately 9 mg, approximately 0.047 mmol) in a THF—$H_2O$ solution (about 8+2 ml) at about 55-60° C. for approximately 1 h, or until TLC analysis ($SiO_2$ plates; hexanes/ethyl acetate/MeOH, approximately 16:6:1; visualization with $KMnO_4$ solution) showed very little starting ester present. The mixture was cooled to room temperature, treated with approximately 50 µl 1N NaOH and concentrated to remove most of the THF. The mixture was extracted with ether/hexanes, approximately 1:1, and the organic extract was dried with $Na_2SO_4$ (anh.). After evaporation of the solvent, the remainder was flash chromatographed with hexanes/ethyl acetate/MeOH, approximately 16:6:1. Two fractions were obtained: a) a first fraction of the starting THPO-ester, approximately 16 mg; and b) a second fraction which was a mixture of ester 1 and lactone 2 (FIG. 1).

The second fraction was chromatographed again with hexanes/ethyl acetate/MeOH, 16:6:1 to furnish 1 (E/Z 86:14, approximately 90 mg, approximately 58%) in the less polar fraction. $^1H$ NMR (600 MHz, $C_6D_6$, δ): 0.79 (d, J=6.6 Hz, $(CH_3)_2$, a 0.91 (d, J=6.6 Hz, $(CH_3)_2$, Z), 2.01-2.08 (m, H-4 E, $CH_2C=C$, Z), 2.46 (t, J=5.4 Hz, OH, E), 2.76 (t, J=6.6 Hz, $CH_2C=C$, E), 3.34 (s, $OCH_3$, E), 3.36-3.38 (m, $CH_2OH$, Z), 3.41 (s, $OCH_3$, Z), 3.70 (q, J=5.4 Hz, $CH_2OH$, E), 4.32 (septet, H-4, Z), 5.71 (br. s, H-2, Z), 5.80 (br. s, H-2, E). $^{13}C$ NMR (151 MHz, $C_6D_6$, E isomer): 21.7 (two carbons), 35.6, 36.7, 51.1, 62.5, 115.6, 167.7, 168.7; Z isomer: 20.9 (two carbons), 29.8, 35.1, 50.8, 61.6, 116.0, 165.7, 166.8.

Lactone 2 (approximately 10 mg) was recovered from the more polar (second) fraction. GC-MS (m/z, relative intensity): 140 ($M^+$, 16), 125 (7), 110 (15), 97 (19), 96 (59), 95 (96), 82 (24), 81 (100), 67 (73), 55 (17), 41 (40). $^1H$ NMR (400 MHz, $C_6D_6$, δ): 0.57 (d, J=6.6 Hz, $(CH_3)_2$), 1.37 (br. t, J=6.5 Hz, $CH_2C=$), 1.70 (septet, J=6.6 Hz, $CH(CH_3)_2$), 3.61 (t, J=6.5 Hz, $CH_2O$), 5.67 (d, J=1.0 Hz, $CHC=$). NMR data are in agreement with ones obtained for this compound in $CDCl_3$ (D'Annibale et al. 2007).

NMR signals of the synthetic compound 1E in $CDCl_3$ were: $^1H$ (400 MHz): 1.12 (d, J=6.8 Hz, $(CH_3)_2$, E), 2.44 (septet, J=6.5 Hz, $CH(CH_3)_2$), 2.87 (t, J=6.4 Hz, $CH_2C=$), 3.73 (s, $OCH_3$), 3.81 (br. q, 5.2 Hz, $CH_2OH$), 5.85 (br. s, CH=). $^{13}C$ (101 MHz): 21.5 (two carbons), 34.7, 36.2, 51.3, 62.0, 115.3, 166.8, 168.7.

At the core of the chosen synthetic route lies a stereoselective carbocupration of α,β-acetylenic esters that was exclusively cis-stereospecific when the reaction was conducted in THF at low temperatures (Corey and Katzenellenbogen 1969, Bourque et al. 1999, Drew et al. 1999). However, a conjugate addition of a heterocuprate, formed in situ from isopropylmagnesium bromide and copper(I) iodide in the presence of N,N,N',N'-tetramethylethylenediamine (Crimmins et al. 1984), to the acetylenic ester (FIG. 1) proceeded with some loss of stereoselectivity resulting in a mixture of E and Z olefinic esters in an approximately 92:8 ratio. During acid-catalyzed removal of the tetrahydropyranyl (THP) protecting group, the ratio of 1E and 1Z dropped to approximately 86:14 and a considerable amount of lactone 2 was formed, thus indicating instability of the putative pheromone in acidic medium. A noticeable cyclization of 1E to 2 occurred also in $CDCl_3$ that was used for recording NMR spectra and known for its residual acidity. Using t-butyldimethylsilyl (TBDMS) protecting group (instead of THP) for the acetylenic alcohol provided a similar stereochemistry at the carbocupration (E/Z 93:7) step but again resulted in significant lactonization when the TBDMS group was removed with highly basic tetrabytulammonium fluoride. Lactonization also occurred when a purified sample of the synthetic (E)-3-(2-hydroxyethyl)-4-methyl-2-pentenoate was injected at 260° C. into the split-splitless injection port of the GC-coupled MS that resulted in a total ion chromatogram comprising 1E,1Z and 2 in a ratio of approximately 39:8:53; the same sample analyzed by cool-on-column GC-MS injection yielded an approximately 88:9:3 mixture of 1E:1Z:2. Because of thermal instability, initial attempts to isolate the putative pheromone by preparative GC equipped with a conventional injection port failed. A purified sample of the synthetic compound stores indefinitely at approximately) degrees to 25° C. in aprotic solvents, such as, for example, benzene, hexane, ethyl acetate, etc.

The synthetic methyl (E)-3-(2-hydroxyethyl)-4-methyl-2-pentenoate was diluted with hexane to approximately 100 ng/µl and about 1 µl of sample was injected on the GC-EAD system described above. An about 1.0 µl injection of approximately 50 ng of linalool and approximately 100 ng/µl of the synthetic methyl (E)-3-(2-hydroxyethyl)-4-methyl-2-pentenoate in hexane was used to determine retention times and test antennal responses. Linalool was previously determined to elicit a consistent antennal response and was co-injected with methyl (E)-3-(2-hydroxyethyl)-4-methyl-2-pentenoate to confirm that the antenna was viable. Antennae from male and female *D. abbreviatus* were used as detectors to confirm antennal response to the synthetic compound.

These experiments enabled us to assign a structure to the active peak as methyl (E)-3-(2-hydroxyethyl)-4-methyl-2-pentenoate (1E). The NMR analysis as shown in Table 2 also revealed an inactive isomer (methyl (Z)-3-(2-hydroxyethyl)-4-methyl-2-pentenoate) and a related lactone 2.

TABLE 2

$^1H$ (600 MHz) and $^{13}C$ (151 MHz) spectroscopic data for the lactoneinactive degradation product of the putative pheromone of *Diaprepes abbreviatus* found in headspace collections

TABLE 2-continued

| Position | δ $^{13}$C [ppm] | δ $^1$H [ppm] |
|---|---|---|
| 2 | 114.08 | 5.80 |
| 4 | 34.8 | 2.47 |
| 5 and 6 | 20.2 | 1.12 |
| 7 | 26.4 | 2.39 |
| 8 | 66.3 | 4.36 |

Only HSQC data are reported for the lactone.
Chemical shifts referenced to δ(CHCl$_3$) = 7.26 ppm for $^1$H and δ(CHCl$_3$) = 77.36 ppm for $^{13}$C.
The degradation product is numbered in the same order as the putative pheromone (Table 1) for comparison.

Figure 3C:
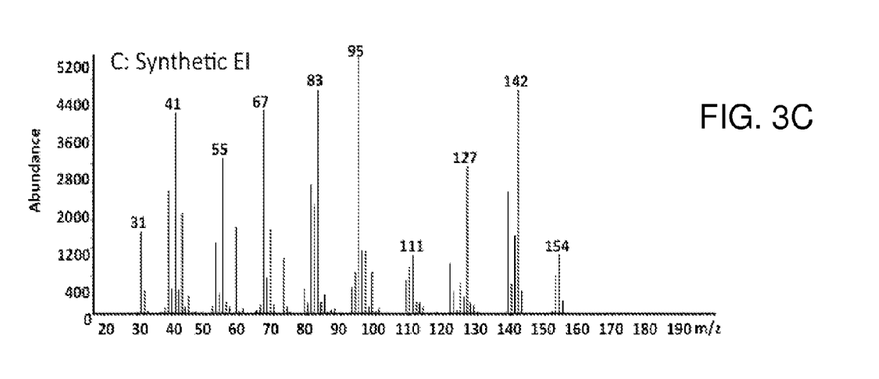

The structure of the synthetic compound was confirmed as identical with the natural compound by mass spectra (FIG. 3C) of both isomers and NMR analysis. As with the natural material, the synthetic material contained a pair of Z/E isomers of the compound methyl 3-(2-hydroxyethyl)-4-methyl-2-pentenoate along with the lactone breakdown product. The NMR of the synthetic sample obtained in C$_6$D$_6$ showed two doublets at approximately 0.79 and 0.91 ppm (corresponding to the doublets at approximately 1.09 and 1.12 ppm in the isolated material) due to a pair of methyl groups from both stereoisomers split by a single proton on the adjacent carbon. Similarly, there was a pair of singlets at approximately 3.34 and approximately 3.41 ppm due to methyl groups from isomeric esters corresponding to the singlets at approximately 3.73 and approximately 3.71 ppm in the NMR of natural sample recorded in CDC$_{13}$. A NOE difference spectrum obtained by irradiating the resonance of the larger doublet at approximately 0.79 ppm resulted in enhancement of the larger singlet from the olefinic proton at approximately 5.80 ppm and vice versa. Therefore, the olefinic proton and the isopropyl group in the major stereoisomer are in the cis (Z) position, and this stereoisomer and the natural product have the trans (E) configuration. Integration of these absorptions and others in the synthetic product confirmed the relative concentrations found during GC-MS analysis of this product.

Example 5

Behavioral response to the pheromone was tested in an olfactometer (Model 4C, ARS, Inc., Micanopy, Fla. USA) wherein individual weevils (starved for about 24 h) were placed in a glass inlet and allowed to walk upwards into the center of an arena with a balanced, filtered and humidified airflow from two arms oriented at 180° to each other and outfitted with glass reservoirs containing an odor source or blank. The assays were conducted in the dark between about 9 AM and 2 PM; each run was terminated when the weevil moved into one of the glass receptacles or when about 15 min had elapsed. Assays were run in the dark because of a strong phototropic response in this insect (Lapointe and Hall 2009). Weevil position was scored as no-response (remaining in the inlet), no-choice (moving to but remaining in the central arena) or choosing one of the two arms. Responses of unmated approximately 4 to 6-week-old males and females were recorded to various odor sources: fresh young citrus leaves (flush), flush fed upon for about 24 hr by male *D. abbreviatus*, approximately 30 μg of methyl (E)-3-(2-hydroxyethyl)-4-methyl-2-pentenoate in approximately 10:1 hexanes:ethyl acetate pipetted onto a glass slide, and a clean glass slide. All glass components of the olfactometer were thoroughly washed between runs with warm soap and water, rinsed with methanol and air-dried. Between replications of a given treatment, the arms of the olfactometer used for that treatment were switched to control for bias in the apparatus. The number of weevils choosing a treatment arm was compared with the control arm (clean air) by the G-test (Sokal and Rohlf 1994).

Figure 4:
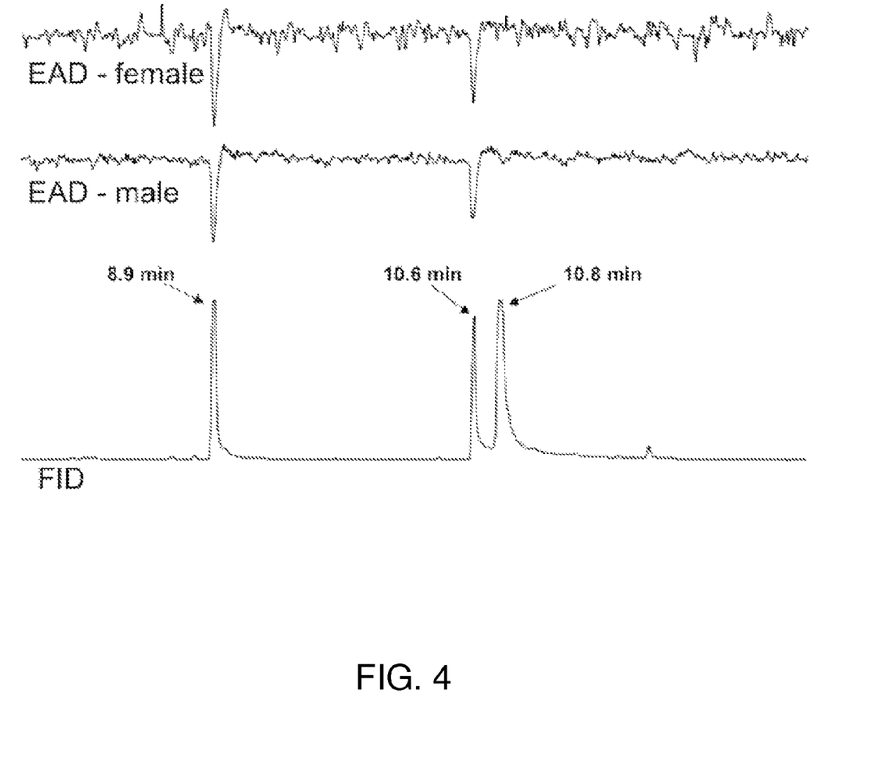
FIG. 4 shows simultaneous gas chromatogram (FID) and electroantennogram detection (EAD) of antennae from a female and a male *Diaprepes abbreviatus* responding to a hexane solution of 50 ng linalool (RT 8.9 min) and 100 ng of synthetic methyl (E)-3-(2-hydroxyethyl)-4-methyl-2-pentenoate (10.6 min) in hexane. The peak at 10.8 min corresponds to the lactone product (2) also shown in FIG. 1.

Both male and female antennae responded to linalool (8.9 min in FIG. 4) and to methyl (E)-3-(2-hydroxyethyl)-4-methyl-2-pentenoate (10.6 min in FIG. 4). Neither responded to the Z isomer (not shown) or the lactone (10.8 min in FIG. 4). In two-choice olfactometer tests, female weevils consistently moved upwind more often (α=0.05, G-test) to the olfactometer arm containing either approximately 30 μg of methyl (E)-3-(2-hydroxyethyl)-4-methyl-2-pentenoate or citrus leaves previously fed upon by males (MFUF) than to clean air (Table 3). Males did not show a clear preference for the pheromone or MFUF compared with clean air. Neither males or females showed a preference when offered a choice between clear air and citrus leaves (flush).

TABLE 3

Behavioral response of *Diaprepes abbreviatus* adults in a two-choice olfactometer

| Sex | Number choosing | | | | Pr > G |
|---|---|---|---|---|---|
| | A | B | No choice | No response | |
| A: Air; B:30 μg methyl (E)-3-(2-hydroxyethyl)-4-methyl-2-pentenoate | | | | | |
| Male | 30 | 34 | 20 | 69 | N.S. |
| Female | 17 | 48 | 17 | 71 | <0.001 |
| A: Air; B: MFUF | | | | | |
| Male | 14 | 15 | 6 | 5 | N.S. |
| Female | 6 | 20 | 13 | 13 | 0.009 |
| A: Air, B: Air | | | | | |
| Male | 12 | 18 | 6 | 32 | N.S. |
| Female | 6 | 9 | 13 | 36 | N.S. |
| A: Air, B: Citrusleaves | | | | | |
| Male | 4 | 4 | 2 | 13 | N.S. |
| Female | 4 | 3 | 7 | 7 | N.S. |

Methyl (E)-3-(2-hydroxyethyl)-4-methyl-2-pentenoate, can also be used as a sole attractant or in combination with plant volatiles, such as those disclosed in U.S. Pat. No. 8,066,979 to Dickens et al., herein incorporated by reference, including one or more of: (a) alcohol and aldehyde monoterpenes (e.g., linalool, citronellal, nerol, and trans-geraniol), (b) green leaf volatiles (e.g., cis-3-hexen-1-ol and trans-2-hexen-1-ol), and (c) an aromatic monoterpenoid (e.g., carvacrol).

Nonlimiting examples of suitable carriers that could support the pheromone and or plant volatiles include, for example, corncob grits, pregel defatted corn grits (PDCG), diatomaceous earth, alumina, silica, clays, other suitable inorganic oxides, polymers, extruded corn, powdered carbohydrates such as corn starch, dextrans and cellulose; and the like. Preferred carriers include diatomaceous earth, alumina, silica, clays.

Other active ingredients, including pesticides, can be included in traps containing the pheromone. Active pesticides can be any substance which kills or inhibits the reproductive capabilities of *D. abbreviatus*. Unlimited examples of active ingredients suitable for use with the attractant composition of the present invention include for example, organophosphates, carbamates, arsenicals, pyrethroids, insect growth regulators, boric acid, silica gel, and borate as disclosed in U.S. Pat. No. 5,104,658, which is herein incorporated by reference. See also, for example, U.S. Pat. No. 5,177,107; herein incorporated by reference. See also U.S. Pat. No. 7,244,607, which is herein incorporated by reference, for a pesticide called GRANDEVO™, a broad spectrum bacterial insecticide for citrus. Preferred the pesticides are those currently used to control adults Diaprepes. These pesticides include Sevin, 1-naphthalenol methyl carbamate; Guthion, phosphorodithioic acid O,O-dimethyl S-[(4oxo-1,2,3-benzotriazin-3 (4H)-yl)methyl]ester; and Orthene, acetylphosphoramidothioic asic O,S-dimethyl ester. These pesticides are currently used in foliar sprays. Soil control pesticides could also be used in a trap along with the pheromone including Bifenthrin, 2-methylbiphenyl-3-ylmethyl 9Z)-(1RS)-cis-3-(2-chloro-3, 3,3,trifluoroprop-1-enyl)-2,2-dimethylcyclopropoanecarboxylate, a pyrethroid.

The carriers for the above discussed insecticides can be the carriers discussed supra.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

REFERENCES

The disclosure of patents and other references cited in the specification are herein incorporated by reference in their entirety.

AMBROGI, B. G., VIDAL, D. M., and ZARBIN, P. H. G. 2009. Feromônios de agregação em Curculionidae (Insecta: Coleoptera) e sua implicação taxonômica. *Quim. Nova* 32: 2151-2158.

BEAVERS, J. B., MCGOVERN, T. P., and ADLER, V. E. 1982. *Diaprepes abbreviatus*: laboratory and field behavioral and attractancy studies. *Environ. Entomol.* 11: 436-439.

BLIGHT, M. M., PICKETT, J. A., SMITH, M. C., and WADHAMS, L. J. 1984. An aggregation pheromone of *Sitona lineatus*. *Naturwissenschaften* 71: 480.

BLIGHT, M. M. and WADHAMS, L. J. 1987. Male-produced aggregation pheromone in pea and bean weevil, *Sitona lineatus* (L.). *J. Chem. Ecol.* 13: 733-739.

BRICHACEK, M. P. and CARLSON, R. M. 2007. Dihydropyran as a template for lactone synthesis. *Synth. Commun.* 37: 3541-3549.

BOURQUE, E., GRENON, M., LALIBERTE, S., and DESLONGCHAMPS, P. 1999. Macrocyclic studies of EZ and ZZ 12-membered aza macrocycles; novel molecular rearrangement observed. *Synlett* 1999: 1115-1117.

BROWNLEE, R. G. and SILVERSTEIN, R. M. 1968. A micro preparative gas chromatograph and a modified carbon skeleton determinator. *Anal. Chem.* 40: 2077-79.

COREY, E. J. and KATZENELLENBOGEN, J. A. 1969. A new stereospecific synthesis of trisubstituted and tetrasubstituted olefins. The conjugate addition of dialkylcopperlithium reagents to α,β-acetylenic esters. *J. Am. Chem. Soc.* 91:1851-1852.

CRIMMINS, M. T., MASCARELLA, S. W., and DELOACH, J. A. 1984. Conjugate addition-cycloacylation of acetylenic diesters: synthesis of highly functionalized cyclopentenones. *J. Org. Chem.* 49: 3033-3035.

D'ANNIBALE, A., CIARALLI, L., BASSETTI, M., and PASQUINI, C. 2007. Synthesis of alkyl-substituted six-membered lactones through ring-closing metathesis of homoallyl acrylates, an easy route to pyran-2-ones, constituents of tobacco flavor. *J. Org. Chem.* 72: 6067-6074.

DICKENS, J. C., JANG, E. B., LIGHT, D. M., and ALFORD, A. R. 1990. Enhancement of insect pheromone responses by green leaf volatiles. *Naturwissenschaften* 77:29-31.

DREW, M. G. B., HARWOOD, L. M., JAHANS, A., ROBERTSON, J., and SWALLOW, S. 1999. Convergent synthesis of the putative biogenic precursor of mycaperoxide B and norsesterterpene triene isolated from an Australian sponge. *Synlett* 1999: 185-188.

GOTTLIEB, H. E., KOTLYAR, V., and NUDELMAN, A. 1997. NMR chemical shifts of common laboratory solvents as trace impurities. *J. Org. Chem.* 62: 7512-7515.

HARARI, A. R. and LANDOLT, P. J. 1997. Orientation of sugarcane rootstalk borer weevil, *Diaprepes abbreviatus*, to weevil, frass, and food odors. *J. Chem. Ecol.* 23: 857-868.

JONES, I. F. and SCHROEDER, W. J. 1984. Capture of *Diaprepes abbreviatus* (Coleoptera: Curculionidae) in frass extract-baited traps in citrus. *J. Econ. Entomol.* 77: 334-336.

LAPOINTE, S. L. 2004. Antecedentes y estrategias para el combate de *Diaprepes abbreviatus*, plaga invasora del Caribe. *Manejo Integrado de Plagas y Agroecologia (Costa Rica)* 71: 106-111.

LAPOINTE, S. L., BORCHERT, D. M., and HALL, D. G. 2007. Effect of low temperatures on mortality and oviposition in conjunction with climate mapping to predict spread of the root weevil *Diaprepes abbreviatus* and introduced natural enemies. *Environ. Entomol.* 36: 73-82.

LAPOINTE, S. L., EVENS, T. J., and NIEDZ, R. P. 2008. Insect diets as mixtures: optimization for a polyphagous weevil. *J. Insect Physiol.* 54: 1157-1167.

LAPOINTE, S. L. and HALL, D. G. 2009. Arrestment behavior in the polyphagous tropical root weevil *Diaprepes abbreviatus*. *J. Econ. Entomol.* 102: 992-998.

MARVALDI, A. E., SEQUEIRA, A. S., O'BRIEN, C. W., and FARRELL, G. D. 2002. Molecular and morphological phylogenetics of weevils (Coleoptera, Curculionoidea): do niche shifts accompany diversification? *Syst. Biol.* 51: 761-785.

OTÁLORA-LUNA, F., HAMMOCK, J. A., ALESSANDRO, R. T., LAPOINTE, S. L., and DICKENS, J. C. 2009. Host plant kairomones for the tropical weevil *Diaprepes abbreviatus*. *Arthropod-Plant Interactions* 3: 63-73.

PETTERRSON, T., EKLUND, A.-M., and WAHLBERG, I. 1993. New lactones from tobacco. *J. Ag. Food. Chem.* 41: 2097-2103.

RAMA RAO, A. V. and REDDY, R. 1986. A simple methodology for the synthesis of 3,4-dihydroisocoumarins. *Synth. Commun.* 16: 97-102.

SCHROEDER, W. J. 1981. Attraction, mating, and oviposition behavior in field populations of *Diaprepes abbreviatus* on citrus. *Environ. Entomol.* 10: 898-900.

SCHROEDER, W. J. and BEAVERS, J. B. 1985. Semiochemicals and *Diaprepes abbreviatus* (Coleoptera: Curculionidae) behavior: implications for survey. *Fla. Entomol.* 68: 399-402.

SEYBOLD, S. J. and VANDERWEL, D. 2003. Biosynthesis and endocrine regulation of pheromone production in the Coleoptera. Pp 137-200 in G. J. Blomquist and R. G. Vogt (eds.). Insect Pheromone Biochemistry and Molecular Biology. Elsevier Academic Press, London, United Kingdom.

SIMPSON, S. E., NIGG, H. N., COILE, N. C., and ADAIR, R. A. 1996. *Diaprepes abbreviatus* (Coleoptera: Curculionidae): host plant associations. *Environ. Entomol.* 25: 333-349.

SOKAL, R. R. and ROHLF, F. J. 1994. Biometry: the principles and practice of statistics in biological research. Freeman, N.Y.

WOLCOTT, G. N. 1936. The life history of "*Diaprepes abbreviatus*" L., at Rio Piedras, Puerto Rico. *J. Agric. Univ. Puerto Rico.* 20: 883-914.

We claim:

1. Methyl (E)-3-(2-hydroxyethyl)-4-methyl-2-pentenoate.

2. A composition comprising methyl (E)-3-(2-hydroxyethyl)-4-methyl-2-pentenoate and a carrier.

3. A method for attracting female root weevils to an object or area comprising: (a) treating said object or area with a female root weevil attracting amount of a composition comprising methyl (E)-3-(2-hydroxyethyl)-4-methyl-2-pentenoate and optionally a carrier or carrier material.

4. A method for at least lessening damage caused by root weevils to one or more trees or plants comprising: (a) deploying in the vicinity of said one or more trees or plants an insect trap baited with a female root weevil attracting amount of methyl (E)-3-(2-hydroxyethyl)-4-methyl-2-pentenoate.

5. The method of claim 4 further comprising providing a pesticide in said trap.

6. A kit for attracting female root weevils comprising a carrier and a female root weevil attracting amount of methyl (E)-3-(2-hydroxyethyl)-4-methyl-2-pentenoate on said carrier.

7. The kit of claim 6 further comprising a second carrier and an insecticide wherein said insecticide is on the second carrier.

* * * * *